(12) United States Patent
Frey et al.

(10) Patent No.: US 9,439,591 B2
(45) Date of Patent: Sep. 13, 2016

(54) ANALYSIS SYSTEM AND METHOD FOR DETERMINING AN ANALYTE IN A BODY FLUID

(75) Inventors: Stephan-Michael Frey, Griesheim (DE); Hans List, Hesseneck-Kailbach (DE); Andrea Rittinghaus, Neckarsteinach (DE); Volker Zimmer, Morbach (DE); Guenter Ihle, Mauer (DE); Wolfgang Roedel, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 727 days.

(21) Appl. No.: 12/962,000

(22) Filed: Dec. 7, 2010

(65) Prior Publication Data

US 2011/0137205 A1 Jun. 9, 2011

Related U.S. Application Data

(63) Continuation of application No. PCT/EP2009/003307, filed on May 9, 2009.

(30) Foreign Application Priority Data

Jun. 7, 2008 (EP) ..................................... 08010403

(51) Int. Cl.
*A61B 5/157* (2006.01)
*A61B 5/15* (2006.01)
(Continued)

(52) U.S. Cl.
CPC ............. *A61B 5/157* (2013.01); *A61B 5/1411* (2013.01); *A61B 5/1455* (2013.01);
(Continued)

(58) Field of Classification Search
CPC ............ A61B 5/1411; A61B 5/15146; A61B 5/14532; A61B 5/150022; A61B 5/150412; A61B 5/150564; A61B 5/15153; A61B 5/15161; A61B 5/15174
USPC ................ 606/181, 183; 600/583, 575, 584; 422/69
See application file for complete search history.

(56) References Cited

U.S. PATENT DOCUMENTS 5,035,704 A * 7/1991 Lambert et al. .............. 606/182
6,607,658 B1 8/2003 Heller et al.
(Continued)

FOREIGN PATENT DOCUMENTS

WO WO 02/00101 A 1/2002
WO WO 2006/092281 A1 9/2006
(Continued)

OTHER PUBLICATIONS

International Search Report dated Jul. 9, 2009 in PCT/EP2009/003307.

*Primary Examiner* — Adam J Eiseman
(74) *Attorney, Agent, or Firm* — Faegre Baker Daniels LLP

(57) ABSTRACT

A system for determining an analyte in a body fluid includes a magazine comprising two partial magazines, one including chambers containing analysis elements having a sample contact zone and a reagent system containing a reagent, whose reaction with the body fluid results in a change of a variable, and another including chambers containing puncturing elements having a tip having a capillary channel, which forms a fluid connection between the tip and a sample transfer zone of the puncturing element. The system may also include an analysis instrument having a puncturing drive for driving a puncturing element on a movement path, a mounting for receiving the magazine such that one chamber of the magazine at a time is located in a functional position, in which a puncturing element in the chamber can be moved by the puncturing drive, and a measuring and evaluation apparatus for measuring the change of the variable.

35 Claims, 7 Drawing Sheets

(51) Int. Cl.
    *A61B 5/145*         (2006.01)
    *A61B 5/1455*       (2006.01)
    *A61B 5/151*         (2006.01)

(52) U.S. Cl.
    CPC ........ *A61B 5/14532* (2013.01); *A61B 5/1513* (2013.01); *A61B 5/150022* (2013.01); *A61B 5/15113* (2013.01); *A61B 5/15123* (2013.01); *A61B 5/15146* (2013.01); *A61B 5/15151* (2013.01); *A61B 5/15163* (2013.01); *A61B 5/150358* (2013.01); *A61B 5/150419* (2013.01); *A61B 5/150435* (2013.01); *A61B 5/150503* (2013.01); *A61B 5/150572* (2013.01)

(56) References Cited

U.S. PATENT DOCUMENTS

| | | | |
|---|---|---|---|
| 2002/0052618 A1* | 5/2002 | Haar et al. | 606/181 |
| 2003/0059350 A1* | 3/2003 | Sacherer | 422/104 |
| 2003/0199789 A1 | 10/2003 | Boecker et al. | |
| 2003/0212345 A1 | 11/2003 | McAllister et al. | |
| 2004/0039303 A1 | 2/2004 | Wurster et al. | |
| 2004/0092842 A1* | 5/2004 | Boecker et al. | 600/575 |
| 2004/0098009 A1 | 5/2004 | Boecker et al. | |
| 2005/0202567 A1* | 9/2005 | Zanzucchi et al. | 436/95 |
| 2006/0196031 A1* | 9/2006 | Hoenes et al. | 29/432 |
| 2006/0272432 A1* | 12/2006 | Belongia | 73/864.63 |
| 2007/0219462 A1 | 9/2007 | Briggs et al. | |
| 2008/0125800 A1* | 5/2008 | List | 606/181 |
| 2008/0200887 A1* | 8/2008 | Haar et al. | 604/322 |
| 2010/0000861 A1* | 1/2010 | Zhong | 204/403.01 |

FOREIGN PATENT DOCUMENTS

| | | |
|---|---|---|
| WO | WO 2007/077212 A | 7/2007 |
| WO | WO 2008016564 A2 * | 2/2008 |

* cited by examiner

ANALYSIS SYSTEM AND METHOD FOR DETERMINING AN ANALYTE IN A BODY FLUID

RELATED APPLICATIONS

The present application is a continuation of and claims priority to PCT/EP2009/003307, filed May 9, 2009, which claims priority to EP 08010403.7, filed Jun. 7, 2008, the entire disclosures of which being hereby expressly incorporated herein by reference.

FIELD OF THE DISCLOSURE

The present disclosure relates to an analysis system for determining an analyte in a body fluid sample obtained by a prick in the skin, comprising a magazine having chambers and a reusable analysis instrument. The chambers of the magazine contain analysis elements having a sample contact zone and a reagent system containing at least one reagent, whose reaction with a body fluid results in a measurable change of a measuring variable, and puncturing elements having a tip for piercing into the skin having a capillary channel, which forms a fluid connection between the tip and a sample transfer zone of the puncturing element. The analysis instrument has a puncturing drive for driving a puncture movement of a puncturing element on a movement path, a mounting for receiving the magazine, and a measuring and evaluation unit for measuring the measurable change of a measuring variable to determine a desired analysis result. The disclosure also relates to a method for producing a wound in a body part for the determination of a body fluid discharging from the wound using an analysis system, which has a magazine having chambers and a reusable analysis instrument.

The disclosure also relates to a magazine having chambers for an analysis instrument. The chambers of the magazine contain analysis elements having a sample contact zone and having a reagent system containing at least one reagent, and puncturing elements having a tip for piercing into the skin having a capillary channel.

BACKGROUND AND SUMMARY OF THE DISCLOSURE

Analytes in a body fluid sample, in particular blood, which is obtained by a wound in the skin of a patient, are determined in many fields of medical analysis. In the case of drawing the body fluid from a body part, preferably from the fingertip, small quantities of the body fluid are sufficient to determine an analyte, for example, the glucose content, for medical and diagnostic purposes. The employed instruments are constructed so that they are readily usable not only by medical technicians, but rather also by laypersons.

Two steps are necessary to determine an analyte in a body fluid sample flowing out of a body part. Firstly a wound must be produced by a prick in the skin of a body part, which can be performed by means of a lancing instrument, for example. In a second step, the body fluid is received and analyzed in an analysis instrument. The use of two instruments operating independently of one another is uncomfortable and cumbersome for the user. Therefore, combined systems have been developed, which unify the two instruments known in the art into one instrument and may execute both steps. The known instruments are relatively large, however.

New developments comprise integrated analysis systems. The typically automated instruments allow a "one-step treatment", so that the user must only apply the system once and can read off the analysis results—without further handling steps.

In a first type of such integrated systems, separate puncturing elements and analysis elements are used. Within a combined piercing and analysis instrument, the required movements for piercing into the skin and for transferring a sample liquid droplet thus acquired onto the analysis system are implemented by means of a movement mechanism integrated in the instrument. The blood transfer from the produced wound to the analysis element is difficult to implement. It is to be considered that modern instruments are to work by means of extremely small blood quantities. Further problems relate to the movement and coupling mechanism of the lancets and puncturing elements.

The problems with the transport of very small blood quantities are reduced and the mechanism of the instrument is simplified if, instead of separate puncturing elements and analysis elements, integrated sample acquisition and analysis elements are used, in which the puncturing element and the analysis element are unified in a disposable unit. Because of these features, systems having such integrated sample acquisition and analysis elements have predominantly been proposed in recent time.

Examples are described in the following publications:
1) WO 2006/092281 A1
2) US 2003/0212345 A1
3) U.S. Pat. No. 6,607,658 B1

The present disclosure is directed to improved systems which are compact in overall size and cost-effectively produced. As such, the disclosed analysis system has the features as claimed.

The analysis system according to the disclosure for determining an analyte in a body fluid sample acquired through a prick in the skin comprises a magazine having chambers and a reusable analysis instrument having a puncturing drive, a mounting for receiving the magazine, and a measuring and evaluation unit.

In its chambers, the magazine contains analysis elements having a sample contact zone and a reagent system containing at least one reagent, whose reaction with the body fluid results in a measurable change of a measuring variable, and puncturing elements having a tip for piercing into the skin having a capillary channel, which forms a fluid connection between the tip and a sample transfer zone of the puncturing element.

The puncturing drive of the analysis system drives a puncture movement of a puncturing element on a movement path, which comprises a propulsion phase in the puncturing direction and, after reaching a reversal point of the puncture movement, a retraction phase opposite to the puncturing direction. The magazine can be received in the mounting of the analysis instrument in such a manner that one chamber of the magazine at a time is located in a functional position, in which a puncture movement in the chamber can be moved by the puncturing drive. The measuring and evaluation unit is set up to measure the measurable change of a measuring variable and to ascertain the desired analysis result.

According to the present disclosure, the magazine comprises two partial magazines, namely a puncturing element partial magazine having puncturing element chambers, which each contain one puncturing element, and an analysis element partial magazine having analysis element chambers, which each contain one analysis element. The puncturing elements and the analysis elements are thus contained in separate chambers—at least in the delivery state of the magazine, preferably always.

The puncturing element chamber has a puncturing element exit opening. The analysis element chamber has a puncturing element entry opening, which is sealed by means of a sealing film. When the magazine is located in the functional position, the two partial magazines are positioned relative to one another or may be brought into a position such that one puncturing element exit opening is adjacent to one puncturing element chamber and one puncturing element entry opening is neighboring to one analysis element chamber such that the two openings align and a puncturing element can be moved from the puncturing element chamber through the puncturing element exit opening and the puncturing element entry opening into the adjacent analysis chamber. The sealing film, which seals the puncturing element entry opening of the analysis element chamber at least in the delivery state, is opened, for example, punctured, before or during the puncture movement of the puncturing element from the puncturing element chamber into the analysis element chamber. Punctured is used as opened hereafter without restriction of the generality.

The piercing and puncturing of the sealing film can preferably be performed by the puncturing element itself. However, the film can also be opened by another element before the puncturing element exits from the puncturing element exit opening.

The two-part magazine having puncturing element partial magazine and analysis element partial magazine permits the differing and sometimes contrary requirements of the analysis elements and puncturing elements to be taken into consideration. The puncturing element can be sterilized separately, for example, using beta radiation, without the analysis elements also being subjected to the radiation. For example, the puncturing element partial magazine can be equipped with puncturing elements before the assembly with the analysis element partial magazine. The puncturing element exit opening is preferably sealed by means of a sterile cling film, so that the puncturing element chambers are sealed. The sealing is preferably executed before the sterilization of the puncturing element partial magazine and after the puncturing element chambers are equipped with a puncturing element. The puncturing element partial magazine is subsequently subjected to the beta radiation, so that all puncturing elements are sterilized. Because the analysis elements having the included reagents are contained in a separate partial magazine, they are not damaged by the radiation during the sterilization of the puncturing element partial magazine.

According to the present disclosure, the movement path of the puncturing element includes a transfer position within the chamber, in which the sample transfer zone of the puncturing element is adjacent to the sample contact zone of the analysis element, in order to produce a fluid connection to transfer a body fluid sample from the puncturing element to the analysis element. A fluid contact between the puncturing element and the analysis element therefore exclusively occurs in the transfer position of the puncturing element, in which it is located in the analysis element chamber. In other positions of the puncturing element on its movement path, no fluid transport to the analysis element can take place. In this manner, an exactly controlled fluid transfer can occur. In addition to the location-dependent control a time-dependent control is also possible. For example, the puncturing element can remain for a specified time in the transfer position, for example, to make possible a fluid transport into the sample transfer zone of the puncturing element, before the puncturing element and the analysis element are neighboring to one another in such a manner that the sample transfer takes place. A force-controlled blood transfer is also possible in a preferred embodiment.

The puncturing element and the analysis element are preferably moved toward one another for this purpose until they preferably contact one another. The relative movement between the two elements can be performed by a transverse movement (in relation to the puncturing direction) of one of the two elements, preferably by a transverse movement of the puncturing element.

In another embodiment, the relative movement between the analysis element and the puncturing element is caused by a pivot movement of the connection element, which is coupled to the puncturing element and produces a connection between the puncturing element and the puncturing drive. The connection element at least partially extends into the puncturing element chamber. The pivot movement of the connection element can be implemented by a control curve of the drive mechanism, for example. A movement of the connection element transversely to the lancing apparatus is also conceivable.

A plurality of steps are executed according to the present disclosure during the production of the two-part magazine, whose sequence can deviate from the sequence specified here or in which the individual steps may be combined and/or executed jointly.

At the beginning of the production process, the two partial magazines are separate from one another. The puncturing element partial magazine is equipped with puncturing elements. Both the puncturing element exit opening and also the connection element entry opening of each puncturing element chamber are sealed by means of a sealing film each. The puncturing elements contained in the puncturing element partial magazine are sterilized in a further step. In another step, the two partial magazines are connected or coupled to one another. The partial magazines may be connected so they are movable relative to one another. The partial magazines are preferably connected to one another in such a manner that a relative rotational movement between them is prevented. The sealing film of the puncturing element exit opening can also seal the puncturing element entry opening of the analysis element partial magazine.

A further method step comprises the sealing of the analysis element chambers of the analysis element partial magazine on its puncturing element entry opening and on its magazine outlet opening by means of a sealing film each. Another production step provides equipping the analysis element partial magazine with analysis elements. The equipping is performed before the complete sealing of the analysis element chambers or before the sealing of one of the openings. The analysis elements are preferably positioned in a mounting in the chambers.

The individual production steps may vary in their sequence, in particular, both partial magazines may be equipped before their connection. During the production, the puncturing element partial magazine should be sterilized when the analysis element partial magazine is still separate.

In one embodiment of the method, the sealing of the puncturing element entry opening of each analysis element chamber by means of a sealing film occurs before the two partial magazines are connected to one another. Both partial magazines are preferably equipped and sealed separately from one another and only subsequently assembled.

In one embodiment of the method, the rotational fixation of the two partial magazines is first produced during use of the magazine in the analysis system or the reusable analysis instrument.

In the case of one-part magazines, which have a common chamber for puncturing element and analysis element, the problem that the radiation used for sterilization can damage the reagents of the analysis elements and make them partially unusable is solved in that the reagent quantity is increased in the analysis element. A sufficient quantity of functional reagents then remains in the analysis element upon the sterilization, so that a determination of an analyte in the fluid sample can be performed. However, the use of an increased reagent quantity results in significant additional costs.

A further feature of separate partial magazines is that no reagent of the reagent system of the analysis elements comes into contact with the puncturing elements, in particular not during the production or storage. Because the reagents are not allowed to enter the skin, it is important that the puncturing elements are not contaminated.

In addition to the possibility of separate production and sterilization, the analysis system according to the disclosure also permits the two partial magazines to be optimized for the respective requirements. The material for the analysis element partial magazine should form a very good water vapor barrier, so that the analysis elements are kept dry. During the use of photometric analysis elements, the material of the partial magazine should be at least partially, preferably completely transparent. The analysis element partial magazine is preferably produced from a transparent, see-through plastic, in any case the transparent area. Polymer materials are suitable, preferably a cycloolefin copolymer, i.e., an amorphous, transparent copolymer based on cyclic and linear olefins, which are also distinguished by a high transparency, good moisture barrier, and high rigidity with little warpage.

The material of the puncturing element partial magazine should not contain additives which impair the puncturing element and its layer, which is typically hydrophilic. The material also should not be damaged by the (beta) radiation used for sterilization of the puncturing elements.

Both partial magazines preferably comprise plastic materials and are preferably produced in the injection molding method. The plastics are selected in accordance with the requirements.

In the context of the disclosure, it has been established that the use of integrated sample acquisition and analysis elements as described in cited documents (1) to (3) has significant disadvantages. The integration results in increased production costs. In addition, there exists the risk of contamination of the lancing tip of the sample acquisition part by reagents of the analysis part. A two-part magazine according to the present disclosure provides separate lancing and analysis elements, but simultaneously allows a compact construction and simple mechanical design.

The magazine according to the disclosure is preferably a drum magazine, which has a puncturing element partial drum and an analysis element partial drum. The use of a magazine drum allows a very compact construction in particular. Magazine drums appear to be the most promising and attractive concept according to the current state of knowledge with respect to the system size, in relation to the number of possible tests for determining the analyte. Alternatively, the magazine can be a (cuboid) linear magazine.

In one embodiment of the magazine having two partial magazines, three barrier films are provided, namely a first, through which a connection element can be coupled onto the puncturing element, a second, which is positioned between the two partial magazines and separates the puncturing element chamber from the analysis element chamber, and a third, through which the puncturing element can exit from the magazine on its (linear) movement path in the puncturing direction. The magazine preferably has four barrier films, so that each front face of the partial magazines is sealed by means of a film.

The present disclosure is explained in greater detail hereafter on the basis of embodiments shown in the figures. The features shown therein may be used individually or in combination to provide embodiments of the disclosure. The described embodiments do not represent a restriction of the generality of the subject matter defined in the claims.

DETAILED DESCRIPTION OF EMBODIMENTS OF THE DISCLOSURE

Figure 1:
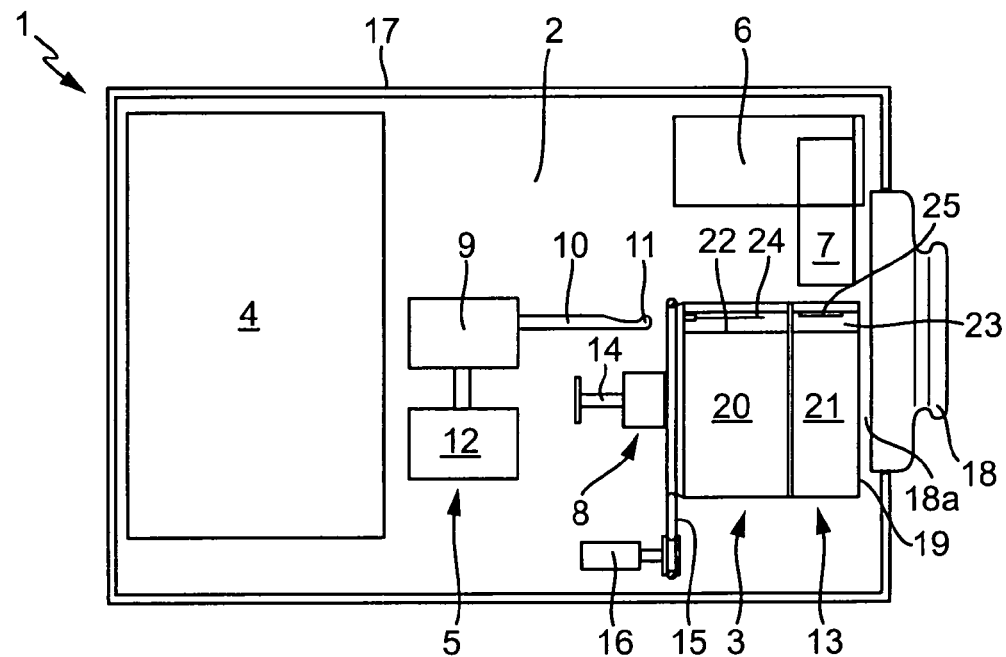
FIG. 1 shows a schematic block diagram of an analysis system comprising an analysis instrument and a magazine.

An analysis system 1 according to the present disclosure comprising an analysis instrument 2 and a magazine 3 is shown in FIG. 1.

The analysis instrument 2 has a power supply 4, a puncturing drive 5, a measuring and evaluation apparatus 6 having an optical measuring unit 7 and a mounting 8 for receiving the magazine 3. The puncturing drive 5 comprises a coupling mechanism 9 having a connection element 10, on whose free end a coupling element 11 is located, and a drive element 12, which is an electric motor. The movement of the drive element 12 is converted into a movement of the connection element 10 and the puncturing element, which is coupled to the connection element 10, so that the puncturing element executes a puncture movement in and opposite to the puncturing direction.

The magazine 3 is preferably implemented as a drum magazine 13, as is also shown in the following figures. The mounting 8 for receiving the magazine 3 comprises a drive shaft 14, which engages in a receptacle (not shown here) of the magazine 3, so that the movement of the shaft 14 is transmitted to the magazine 3. The drive shaft 14 is driven via a belt drive 15 by a motor 16.

The analysis instrument 2 comprises components (not shown here), such as a processor which controls the individual elements and ensures the desired method sequence The analysis instrument 2 has a housing 17 having a skin contact ring 18, on which a fingertip is laid, in order to produce a wound in the skin. The puncturing element 3 exits (preferably partially) from the magazine 3 and then through the skin contact ring 18 out of the analysis instrument 2 and pricks into the skin. The magazine 3 is mounted in the mounting 8 in such a manner that a distance 18*a* is provided between the front face 19 of the magazine 3 in the puncturing direction and the skin contact ring 18. The distance 18a is already required because the puncture of a film which covers the front face 19 is to be performed chronologically and spatially separate from the piercing into the finger. With respect to the desired compact construction of the analysis instrument 2, the axial length of this intermediate space (i.e., the distance 18a) is minimized. It is preferably at most 5 mm, very preferably at most 2 mm, and particularly preferably at most 1 mm.

The drum magazine 13 is a two-part magazine 3 having a puncturing element partial magazine 20 and an analysis element partial magazine 21. The puncturing element partial magazine 21 has adjacent puncturing element chambers 22, in each of which a puncturing element 24, which is oriented in the axial direction of the drum, is contained. The analysis element partial magazine 21 comprises adjacent analysis element chambers 23, in each of which an analysis element 25 is contained. The two partial magazines 20, 21 of the magazine 3 are implemented in such a manner that the puncturing element chambers 22 and the analysis element chambers 23 are different from one another.

In FIG. 1, the magazine 3 is mounted in a functional position in the mounting 8 in which the connection element 10 can be coupled onto a puncturing element 24 in a puncturing element chamber 22. When a piercing into the skin has been completed and the connection element 10 has been moved back out of the puncturing element chamber 22, the magazine 3 is rotated further around its rotational axis until the next, preferably adjacent puncturing element chamber 22 is positioned in such a manner that the connection element 10 can couple onto the puncturing element 24 located in the chamber. The magazine 3 is then again in the functional position.

The magazine 3 can also be positioned in the functional position in such a manner that the optical measuring unit 7 is adjacent to the analysis element chamber 23. The magazine 3 or the two partial magazines 20, 21 are preferably positioned in such a manner that the analysis element chamber 23, which is adjacent to the measuring unit 7, aligns with the puncturing element chamber 22, into which the connection element 10 can be moved. A photometric measurement on photometric analysis elements 25 has the advantage that a very small, cost-effective test field can be used for the measurement, and only small blood quantities are required for the analysis. In addition, the drum 13 is simple to be positioned in front of the photoelectric measuring unit 7.

The photoelectric measuring unit 7 is positioned radially to the analysis element chamber 23 in such a manner that its optic is oriented perpendicularly to the lateral surface 13a of the drum magazine 13 and a change of the measured values in the analysis element 25 can be photometrically measured. The analysis element partial magazine 21 has a transparent area 73 on its lateral surface 13a, so that the measuring unit 7 can detect the change of the measuring variable through the transparent area 73 (preferably when the magazine 3 is in the functional position). The analysis element 25 is positioned to the transparent area 73 (such as a transparent window) in such a manner that a photometric measurement can be performed. The entire lateral surface 13a is preferably transparent. The lateral surface 13a of the drum magazine 13 has planar sections (surface section 76) in such a manner that they are parallel to the analysis elements 75 and the optic of the measuring unit 7. The planar surface sections 76 comprise the transparent area 73 or are completely see-through (transparent). The puncturing element partial magazine 20 preferably also has planar surface sections 76.

Figure 2:
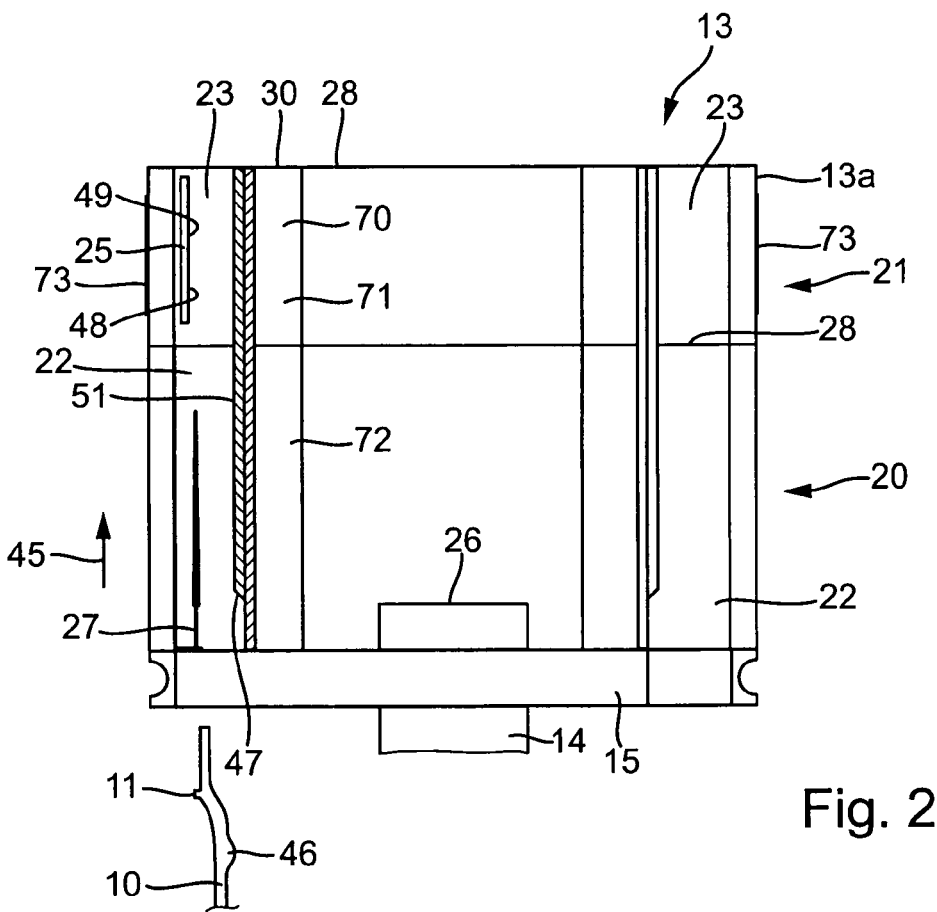
FIG. 2 shows a detail view of a first embodiment of a magazine.
Figure 3:
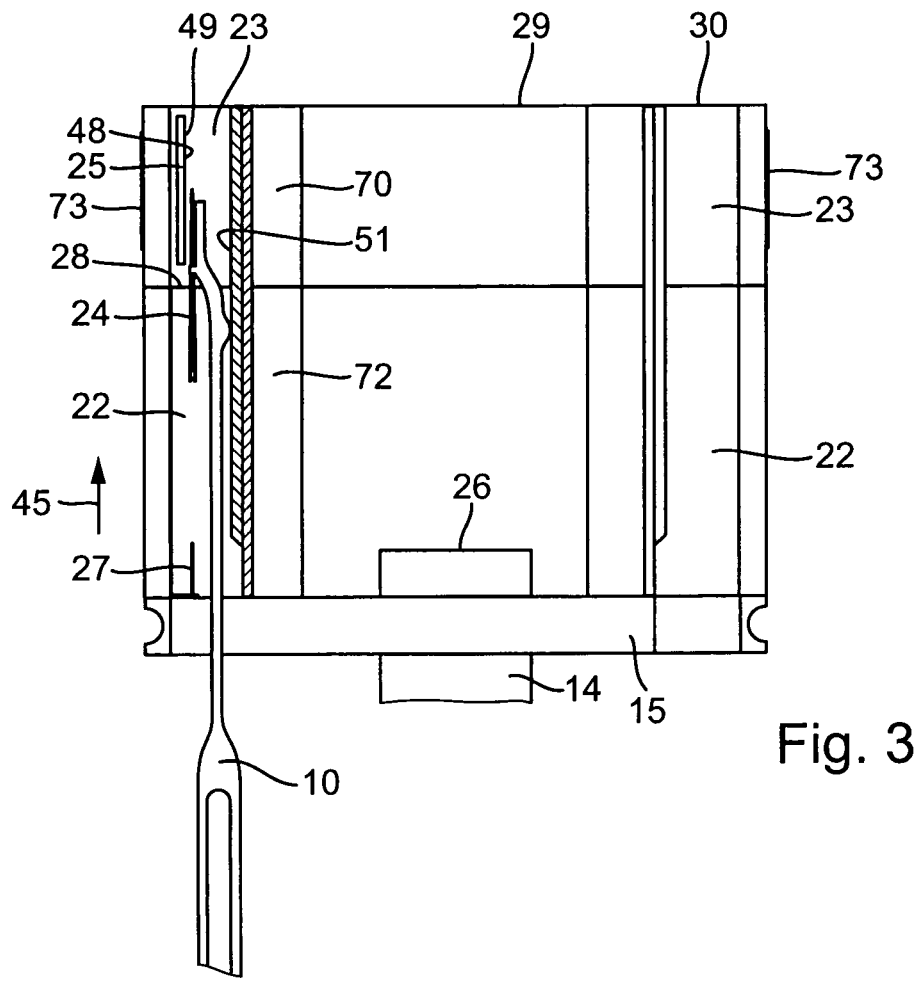
FIG. 3 shows a further view of the magazine from FIG. 2.

FIGS. 2 and 3 show the magazine 3 according to the present disclosure in its functional position, into which it was rotated using the drive shaft 14, which engages in a receptacle 26 of the magazine 3. The receptacle 26 and the upper end of the drive shaft 14 are preferably implemented as a gear ring or gearwheel, respectively, and form a gearwheel connection, which allows reliable and precise positioning of the magazine. In FIG. 2, the connection element 10 of the puncturing drive 5 is positioned outside the magazine 3, in FIG. 3, the puncturing element 24 has been moved on its movement path into a position approximately parallel to the analysis element 25.

The two partial magazines 20, 21 of the cylindrical drum magazine 13 are fixedly connected to one another in the embodiment according to FIGS. 2, 3. A sealing film 28 is positioned between them, which is applied and/or glued or welded onto the respective front sides of the partial magazines 20, 21. The sealing film 28 separates the puncturing element chambers 22 and the analysis element chambers 23. It seals a puncturing element entry opening 32 of the analysis element chamber 23 and simultaneously a puncturing element exit opening 33 of the puncturing element chamber 22.

The analysis element partial magazine 21 is preferably covered on its front end 29 in the puncturing direction with a film 30 in such a manner that magazine outlet openings 31 of the analysis element chambers 23 are sealed on the front side 19. A completely sealed analysis element chamber 23 thus results. The sealing films 28, 30 of the analysis element chamber 23 form a water vapor barrier. All films share the feature that they are as easy as possible to tear further after the puncturing, so as not to obstruct the puncturing element 24 on its movement path and not touch the puncturing element 24 during the retraction phase of the puncture movement, in order not to wipe blood off of the puncturing element 24.

The analysis element 25 is mounted in the analysis element chamber 23 in a mounting (not shown here). The analysis element 25 is preferably positioned in a fluid transfer position, which is fixed in the axial direction (puncturing direction). Because of its mounting and the small dimensions of the analysis element 25, it can be mounted with play. However, its position in the puncturing direction is fixed, so that a fluid transfer is possible from the puncturing element 24 to the analysis element 25.

In one exemplary embodiment, the puncturing element chamber 22 is also covered on the rear end 35 of the magazine 3 in the puncturing direction with a sealing film 36, so that a connection element entry opening 34 of the puncturing element chamber 22 is sealed. The sealing film 36 is opened—preferably by means of the connection element 10—before the puncture movement, in order to allow the entry of the connection element 10 into the puncturing element chamber 22. The puncturing element chamber 22 is hermetically sealed by the two sealing films 28, 36. It is thus ensured that the sterility of the puncturing element 24 is maintained during the storage. The films 28, 36 must therefore not be damaged by the sterilization process.

Figure 4:
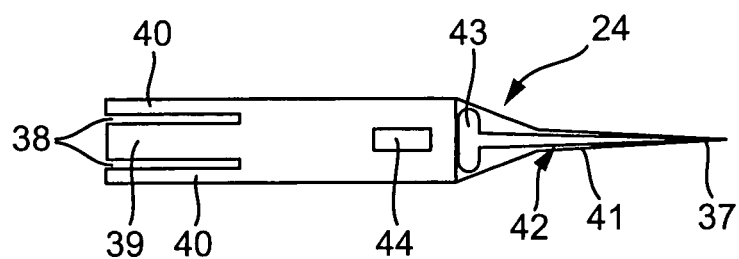
FIG. 4 shows a detail view of a puncturing element.

The puncturing element 24, which is shown in detail in FIG. 4, is clamped in a puncturing element mounting 27 of the puncturing element chamber 22. The puncturing element 24, which is preferably implemented as flat, has a tip 37 and two slots 38 on its end opposite to the tip 37, in such a manner that a central tongue 39 and two edge tongues 40 are formed. The tongues 39, 40 may be elastically bent so that the puncturing element 24 can be placed on the puncturing element mounting 27, which is preferably implemented as a tapered lug. The puncturing element 24 is positioned and securely mounted before and after performance of the puncture movement in the mounting position in the puncturing element mounting 27. The preferably flat puncturing element 24 can be produced by etching and is correspondingly cost-effective. Complex bending procedures for shaping are not necessary.

A capillary channel 41 extends from the tip 37 of the puncturing element 24 on a flat side up to a sample transfer zone 42. The capillary channel 41 can also be open on both sides, e.g., it can be implemented as a (continuous) slot. The sample transfer zone 42 is a spatial area inside the capillary channel 41, which can come into contact with a sample contact zone of an analysis element 25 in the transfer position. In one embodiment, the capillary channel 41 extends beyond the sample transfer zone 42 into a sample excess zone 43 ("waste zone"). This embodiment of the puncturing element 24 permits a transfer of a body fluid preferably only when a first partial quantity of the body fluid, which was first received in the capillary channel 41 after the piercing into the skin, has passed the sample transfer zone 42 and is located in the sample excess zone 43. A second partial quantity of the body fluid sample is located (at the moment) in the sample transfer zone 42, so that the second partial quantity is transferred to a sample contact zone of an analysis element 25. A chronologically controlled sample transfer is thus possible.

The puncturing element 24 has a coupling structure implemented as a coupling receptacle 44, which is implemented as an opening, for example. The corresponding coupling element 11 of the connection element 10 engages in the coupling receptacle 44 to produce a formfitting connection, so that the puncturing element 24 can be moved on its movement path. A preferably bidirectionally acting coupling of the puncturing element 24 to the puncturing drive 5 is thus caused.

The fundamental movement sequence is described by means of FIGS. 2 and 3. Specific movements for other embodiments are explained on the basis of FIGS. 5, 6, and 8. Starting from FIG. 2, the connection element 10 is moved in the puncturing direction 45 (arrow direction). The connection element 10, which is implemented as a pushrod, for example, is guided from the rear end 35 to the magazine 3 and punctures the film 36, in order to penetrate into the puncturing element chamber 22 through the connection element entry opening 34. During the further movement of the connection element 10, a guide cam 46 of the connection element 10 is guided on a ramp 47 in the puncturing element chamber 22 in such a manner that the coupling element 11 engages in the coupling receptacle 44 of the puncturing element 24 and couples the connection element 10 on the puncturing element 24 (in its mounting).

On the further, at least partially linear movement path in the puncturing direction 45, the puncturing element 24 punctures the sealing film 28 between the partial magazines 20, 21, while it is moved through the puncturing element exit opening 33 and the puncturing element entry opening 32 into the analysis element chamber 23, until it finally partially exits through the magazine outlet opening 31 from the magazine 3 and punctures the film 30. This preferably largely linear propulsion phase of the puncture movement ends in the reversal point, at which the puncture into the skin takes place. The reversal point is followed by a retraction phase opposite to the puncturing direction 45. At least a part of the propulsion phase of the puncture movement is performed as a rapid puncture movement, the puncture of the sealing film 28 between the two partial magazines 20, 21 preferably occurring slowly. It can be provided that the puncturing element is stopped between a slow phase and a rapid phase of the propulsion phase, but this is not compulsory.

The magazine 3 is implemented in such a manner that the puncturing element 24 is guided in the magazine 3 during the entire puncture movement. The guiding is preferably caused by the puncturing element partial magazine 20. A puncturing element 24, which exits by means of its tip 37 from magazine 3 and produces a wound, is positioned still having its rear end in the puncturing element chamber 22. The puncturing element 24 extends through the entire analysis element chamber 23, whose length is accordingly significantly less than the length of the puncturing element chamber 22. The guide of the puncturing element 24 on its movement path is defined by the chamber side wall 51 (wall) of the puncturing element chamber 22, for example, in that the connection element 10 is supported (for example, using its guide cam 46) on the wall of the chamber 22.

After the puncturing element 24 has exited from the magazine 3 and has pierced into the skin of a fingertip pressed against the skin contact ring 18, the puncturing element 24 is moved (during the retraction phase) into a transfer position inside the analysis element chamber 23, FIG. 3.

After the generation of the piercing wound, body fluid (blood) from the wound is received in the capillary channel 41 and transferred by capillary forces to the sample transfer zone 42 of the—preferably hydrophilized—puncturing element 24. In the transfer position, a first partial quantity of the body fluid has already passed the sample transfer zone 42 and a second partial quantity has reached the sample transfer zone 42. Because the first partial quantity can be contaminated by sweat, for example, it is not used for analysis.

The analysis element 25 positioned in the fluid transfer position in the axial direction has a sample contact zone 48, which preferably encloses a surface 49 oriented in the puncturing direction, which extends approximately parallel to the puncturing direction 45. The fluid contact between the puncturing element 24 and the analysis element 25 is preferably produced by contacting the surface 49 of the sample contact zone 48 with the sample transfer zone 42 of the puncturing element 24.

In order to overcome the distance 50 between the sample contact zone 48 and the sample transfer zone 42, a relative movement is preferably performed between analysis element 25 and puncturing element 24. The distance 50 is preferably at most 1 mm, more preferably at most 0.5 mm, and particularly preferably at most 0.3 mm. This relative movement can be a transverse movement, for example. One possibility for executing the transverse movement is a displacement or pivoting of the connection element 10.

After the transfer of the body fluid onto the sample contact zone 48, a photometric measurement (such as reflection photometry, absorption measurement, or fluorescence measurement) is performed. Alternatively, an electrochemical measurement (such as amperometry, potentiometry) can be performed.

The puncturing element 24 is subsequently moved back into its mounting position and positioned in the puncturing element mounting 27. The connection element 10 is decoupled from the puncturing element 24 and moved out of the magazine 3.

The relative movement between the puncturing element 24 and the analysis element 25 is preferably caused in that a contact pressure element is pressed transversely to the puncturing direction against the puncturing element 24 positioned in the transfer position. A possible embodiment of such a contact pressure element is described in following FIGS. 5 to 7. Alternatively, a contact pressure element outside the analysis element partial magazine 21 on its front end 29 can also move a protruding puncturing element 24 transversely to the puncturing direction, in order to cause a contact with the analysis element 25.

Figure 5:
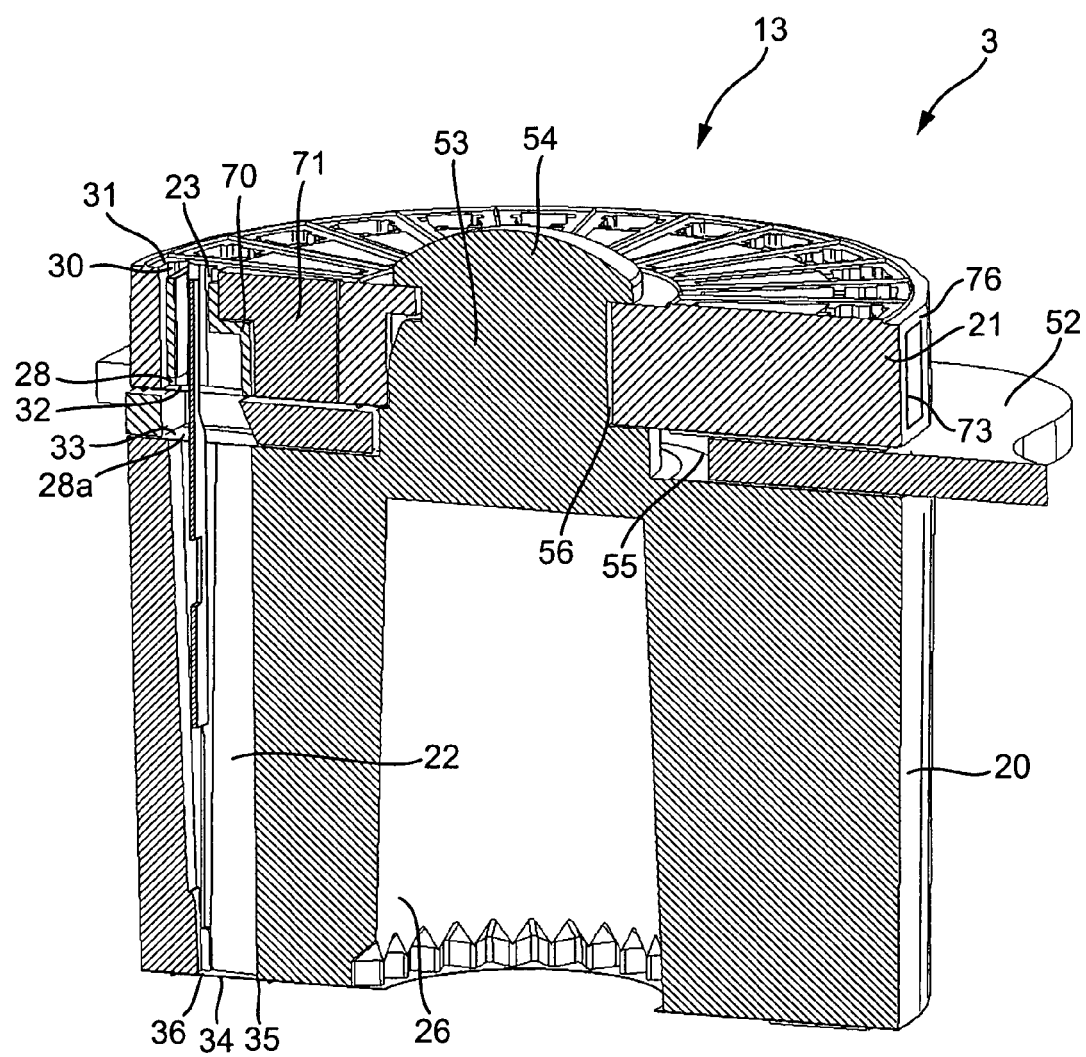
FIG. 5 shows a further embodiment of a magazine having a contact pressure element.
Figure 6:
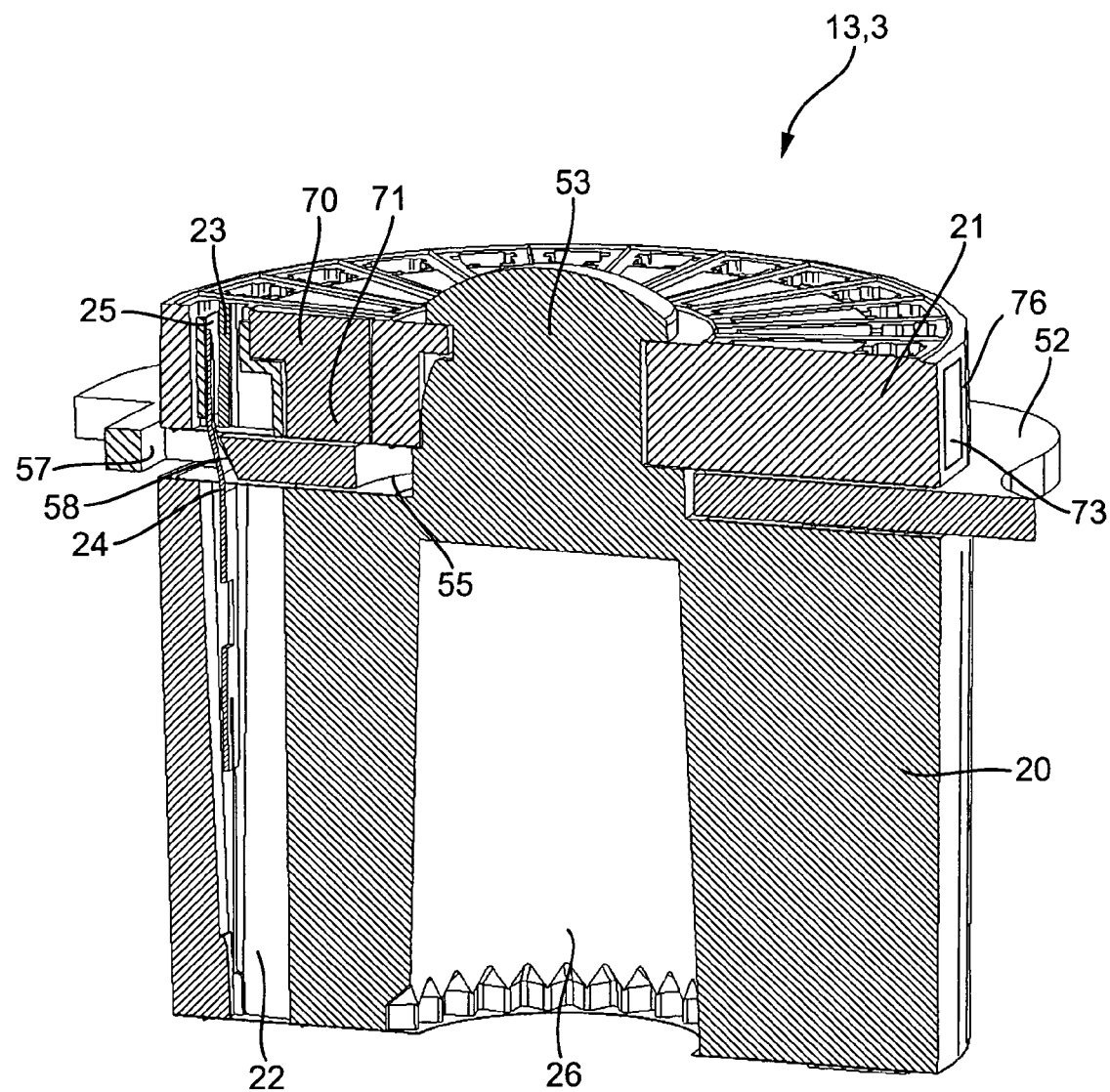
FIG. 6 shows a detail view of the magazine from FIG. 6.

FIGS. 5 to 7 show an alternative embodiment of a magazine 3 according to the present disclosure, which is also a drum magazine 13. The puncturing element partial magazine 20 and the analysis element partial magazine 21 are spaced apart from one another in such a manner that a contact pressure element 52 is positioned between them.

The puncturing element partial magazine 20 has a receptacle 26, partially implemented like a gear ring, on its rear end 35 for the drive shaft 14 (not shown here). In extension of the receptacle 26, the puncturing element partial magazine 20 has a mandrel 53 having a (protruding) sleeve head 54. The mandrel 53 extends through a through opening 55 of the contact pressure element 52 and an opening 56 of the analysis element partial magazine 21. The sleeve head 54, which is widened relative to the opening 56, protrudes out of the magazine 3 and connects the two partial magazines 20, 21 and the contact pressure element 52 in such a manner that they cannot be detached from one another. The mandrel 53 and the opening 56 preferably correspond, in order to generate a fixed (rotationally fixed and radially and axially fixed) connection between the partial magazines 20, 21. A relative movement between the two partial magazines 20, 21 is prevented.

In contrast to the embodiment according to FIGS. 2 and 3, the partial magazines 20, 21 are positioned in such a manner that the puncturing element entry opening 32 and the puncturing element exit opening 33 are spaced apart from one another. Both openings 32, 33 are therefore sealed by means of separate sealing films 28, 28*a*. The film 28*a* is preferably punctured before or during the puncture movement of the puncturing element, preferably by the puncturing element 24 itself.

Figure 7A:
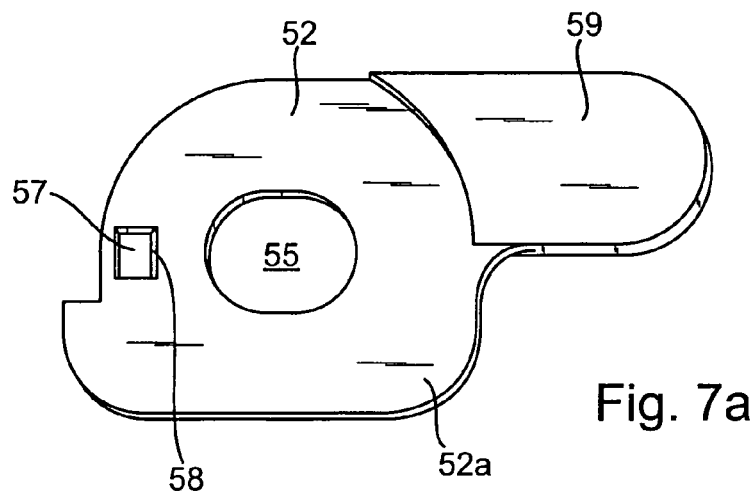
FIGS. 7*a, b, c* show detail views of a contact pressure element from FIG. 5.
Figure 7B:
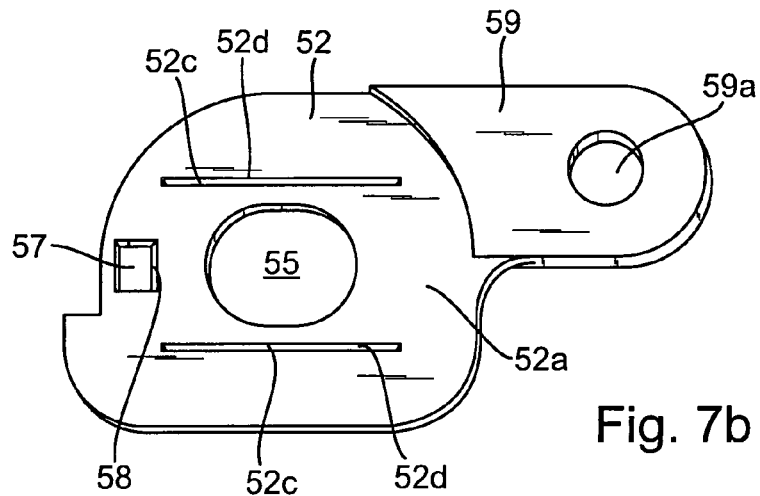
Figure 7C:
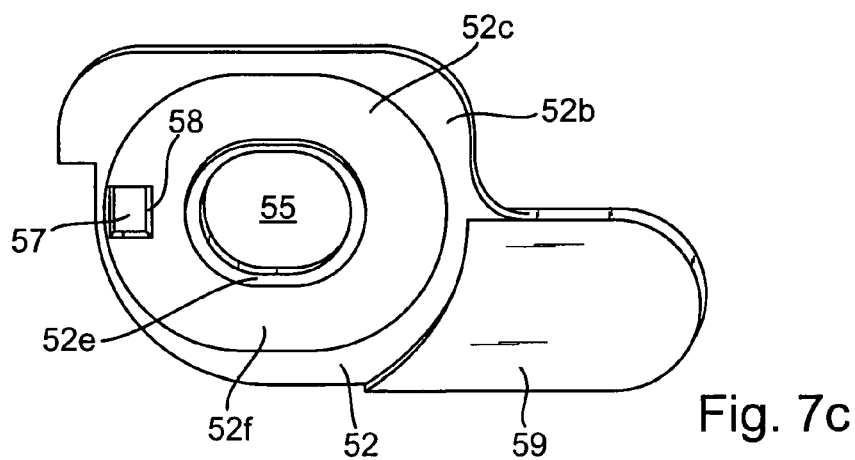

The through opening 55 of the contact pressure element 52 is preferably an oblong hole, as shown in FIGS. 7*a-c*. The oblong hole allows a movement of the contact pressure element 52 in the radial direction between the two partial magazines 20, 21. It is preferably moved (and guided) by the analysis instrument 2, wherein a movement element (not shown) preferably engages on the tongue-like projection 59. The rotational movement of the drum magazine 13 and the translational movement of the contact pressure element 52 in the radial direction (transversely to the puncturing direction) are completely decoupled. The plate-shaped contact pressure element 52 has a puncturing element guide opening 57 having a preferably beveled contact pressure surface 58, which is formed by a side wall of the puncturing element guide opening 57.

In one embodiment of the plate-shaped contact pressure element 52 according to FIG. 7*b*, guide structures 52*c* are positioned on its top side 52*a*, which contact the analysis element partial magazine 21. The guide structure 52*c* is implemented as a guide rail 52*d*. The contact element 52 only touches the partial magazines 21 at the ribs 52*d*, so that the friction during the movement of the contact pressure element 52 is significantly reduced. A defined distance is simultaneously achieved between the top side 52*a* and the analysis element partial magazine 21. Possibly protruding film parts of the sealing film of the analysis element partial magazine 21 may extend into the intermediate space (gap) without obstructing the relative movement between contact pressure element 52 and partial magazine 21. A guide structure 52*c* is preferably also implemented on the bottom side 52*b*, e.g., as a guide rail 52*d* or rib, whereby the friction is further reduced and the contact pressure element 52 is mounted in a defined position between the two partial magazines 20, 21.

In an alternative embodiment according to FIG. 7*c*, the guide structure 52*c* is implemented on the bottom side 52*b* of the contact pressure element 52 as a receptacle chamber 52*f*. The receptacle chamber 52*f* extends around the edge of the through opening 55. An edge elevated in relation to the depression of the receptacle chamber 52*f*, which can be a bead 52*g*, for example, is formed between the receptacle chamber 52*f* and the through opening 55. The friction during rotation of the magazine drum 13 relative to the contact pressure element 52 is reduced. Film parts protruding from the open sealing film 28*a* of the puncturing element exit opening 33 may extend into the depressed receptacle chamber 52*f*, without influencing the movement between the contact pressure element 52 and the partial magazines 20, 21. The force to be applied for the rotation of the magazine 3 in the mounting 10 can thus be reduced, which minimizes the energy consumption, because the contact pressure element 52 is positioned rotationally-fixed in relation to the analysis instrument 2 (only a translational linear movement of the contact pressure element 52 is possible in relation to the analysis instrument 2).

The tongue-like projection 59 can have a handle groove 59*a*, which offers the user a grasping capability during insertion of the magazine 3 in the mounting 10 of the analysis element 2. Touching of the transparent areas or the lateral surface is prevented, which could later corrupt an optical measuring result.

In a further embodiment, the magazine 3, preferably the contact pressure element 52, has a coding, by means of which information about an evaluation curve or evaluation function for converting the measured values into the desired analytical results may be coded. Because the evaluation function or evaluation curve is typically production-batch-specific for the individual analysis elements, the information required for the evaluation may be contained in the coding. The coding can be implemented in the form of a code, such as a barcode (2-D barcode) or in the form of a transponder, such as an RFID transponder (radio frequency identification transponder).

In the lancing position, in which the drum magazine 13 is located at the beginning of the lancing procedure, the puncturing element partial magazine 20 and the analysis element partial magazine 21 are oriented in such a manner that a puncturing element chamber 22, an analysis element chamber 23, and the puncturing element guide opening 57 align. The puncturing element 24 can be moved unobstructed through the puncturing element guide opening 57 of the contact pressure element 52 and performs the puncture movement described on the basis of FIGS. 2 and 3. As soon as the puncturing element 24 is in its transfer position, a relative movement is executed transversely to the puncturing direction between the puncturing element 24 and the analysis element 25 for producing a fluid contact.

FIG. 5 shows the puncturing element 24 in a transfer position after the completed piercing. In this position, the puncturing element 24 extends into the analysis element chamber 23 and into the puncturing element chamber 22 and through the puncturing element guide opening 57. The contact pressure element 52 is in its starting position.

FIG. 6 shows the contact pressure element 52 displaced radially outward (away from the rotational axis of the magazine in the direction of the measuring unit). In this contact pressure position, the contact pressure surface 58 of the puncturing element guide opening 57 presses against the puncturing element 24 and bends it elastically in such a manner that the sample transfer zone 42 of the puncturing element 24 comes into contact with the sample contact zone 48 of the analysis element 25 and a fluid transfer takes place between them.

When the two elements 24, 25 are in contact, the analysis element 25 is preferably positioned in an analysis position, in which an optical detection of a measuring variable is possible. If the analysis element 25 is mounted in its mounting with play in the transverse direction to the puncturing direction, it has reached a defined analysis position upon contact with the puncturing element 24 in any case, which does not permit play transversely to the puncturing direction.

After the analysis of the body fluid sample, the contact pressure element 52 is moved back radially into its starting position. The (elastic) puncturing element 24 re-assumes its original form again. The movement path is continued during the retraction phase.

In an alternative embodiment of the magazine 3 according to the disclosure having an analysis element partial magazine 21 and a puncturing element partial magazine 20, the two partial magazines 20, 21 are movable relative to one another transversely to the puncturing direction.

Figure 8:
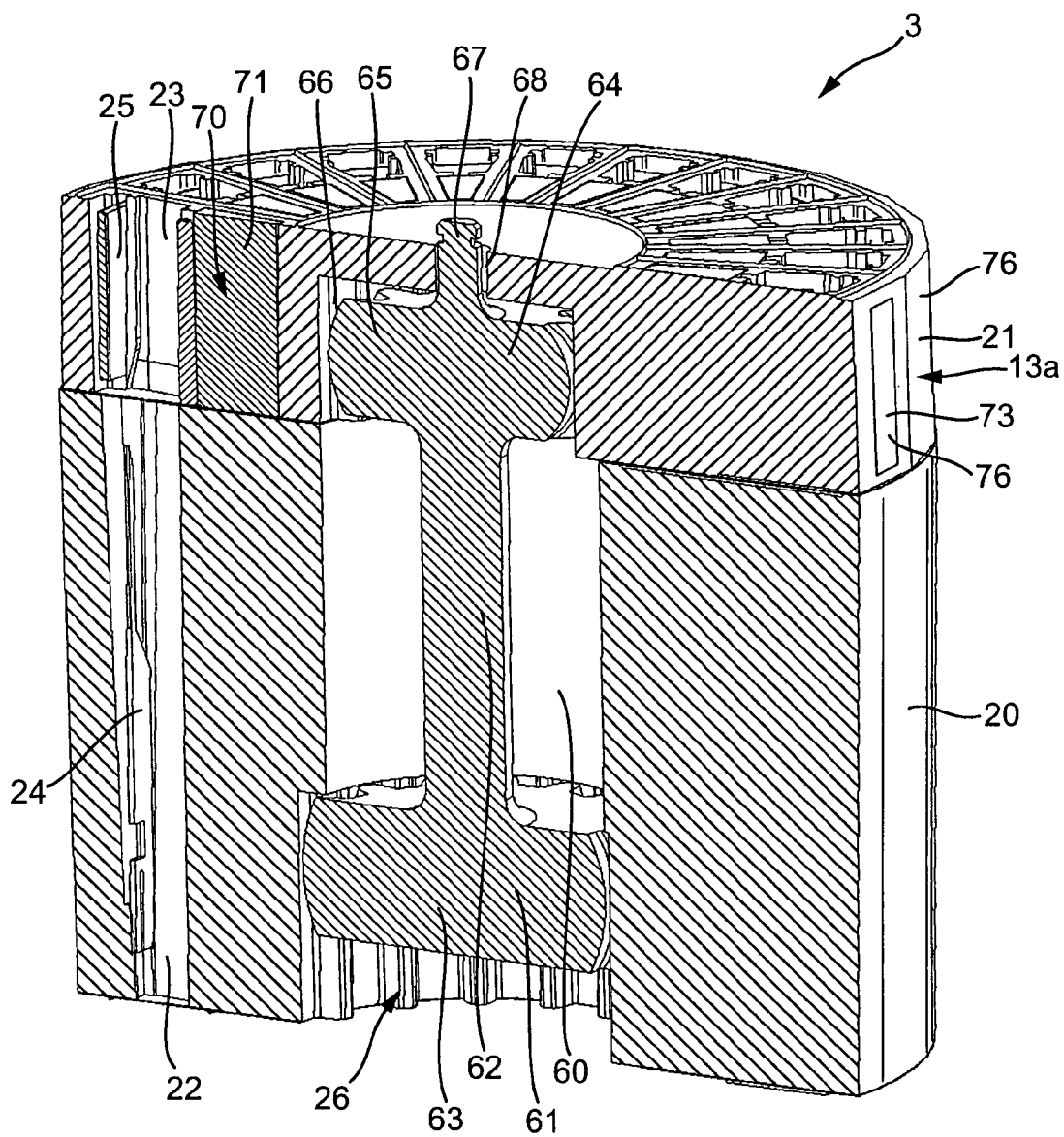
FIG. 8 shows a further embodiment of a magazine.

Another embodiment of such a magazine 3 implemented as a two-part drum magazine 13 is described on the basis of FIG. 8. As in the exemplary embodiment of FIGS. 5 and 6, the two partial magazines 20, 21 are also covered on their respective front sides with films 28, 28a, 30, 36 in this magazine 3, so that the corresponding openings of the chambers 22, 23 are sealed.

In one embodiment of the present disclosure, the films 28, 28a, 30, 36 for sealing the openings 31, 32, 33, 34 of the chambers 22, 23 are glued in a hot-melt adhesive method by means of a hot-melt adhesive to the front sides of the partial magazines 20, 21. The openings of the chambers 22, 23 preferably have hot-melt adhesive receptacle recesses, in which excessive adhesive (hot-melt adhesive) can be received. The hot-melt receptacle recesses may be implemented as depressions, for example, which border the edge of the openings 31, 32, 33, 34. However, reservoirs extending into the magazine interior may also be provided.

The two partial magazines 20, 21 are located so that one puncturing element chamber 22 aligns with one analysis element chamber 23 each. The two partial magazines 20, 21 are positioned rotationally fixed to one another. In other words: the two partial magazines 20, 21 may not be pivoted in relation to one another.

The puncturing element partial magazine 20 has a through opening 60, in which a receptacle 26 is integrated in order to receive a drive shaft (cardan shaft) 14 of the analysis instrument 2. The lower end 61 of a hinge shaft 62 similar to a propeller shaft is also positioned in the gear-ring-shaped receptacle 26. A lower hinge shaft head 63 of the hinge shaft 62 is implemented as a gearwheel and engages in the gear-ring-shaped receptacle 26. An upper gearwheel-shaped hinge shaft head 65 is positioned at the upper end 64 of the hinge shaft 62, which engages in a hinge shaft receptacle 66, similar to a pocket hole, of the analysis element partial magazine 21.

Above the hinge shaft head 65, a pin-like extension 67 is formed, which protrudes through a front wall opening 68 in the front wall of the analysis element partial magazine 21. A cotter pin can be clipped into a groove of the extension 67 positioned outside the magazine 3, so that the hinge shaft 62 cannot be removed from the magazine 3. The two partial magazines 20, 21 are connected rotationally fixed to one another via the hinge shaft 62 and are additionally axially fixed, i.e., a relative movement of the partial magazines 20, 21 in the axial direction is prevented.

The analysis element partial magazine 21 and the puncturing element partial magazine 20 are preferably movable relative to one another transversely to the puncturing direction, in particular radially movable. The hinge shaft 62 may be moved in the hinge shaft receptacle 66 in such a manner that a radial displacement is possible transversely to the puncturing direction. The position of the analysis element 25 in the radial direction can be changed by the relative movement of the two partial magazines 20, 21 to one another in such a manner that a contact is caused between the analysis element 25 and the puncturing element 24, which is positioned in the transfer position. The relative movement comprises a transverse movement path (offset), preferably of at least 0.1 mm, very preferably at least 0.3 mm, particularly preferably at least 0.5 mm. The offset can also be up to 1.5 mm. The relative movement can be caused, for example, by a movement mechanism engaging on the extension 67 or by a lateral tappet pressing on a partial magazine 20, 21 or a similar mechanism. The analysis element partial magazine 21 is preferably moved. An optical evaluation of the analysis element 25 is preferably performed in this radially displaced (deflected) position.

After the transfer of the body fluid, the analysis element partial magazine 21 is moved back into its starting position, so that the analysis element chamber 23 aligns with the puncturing element chamber 22 again. The optical evaluation of the analysis element 25 can alternatively also be performed in this starting position.

Figure 9:
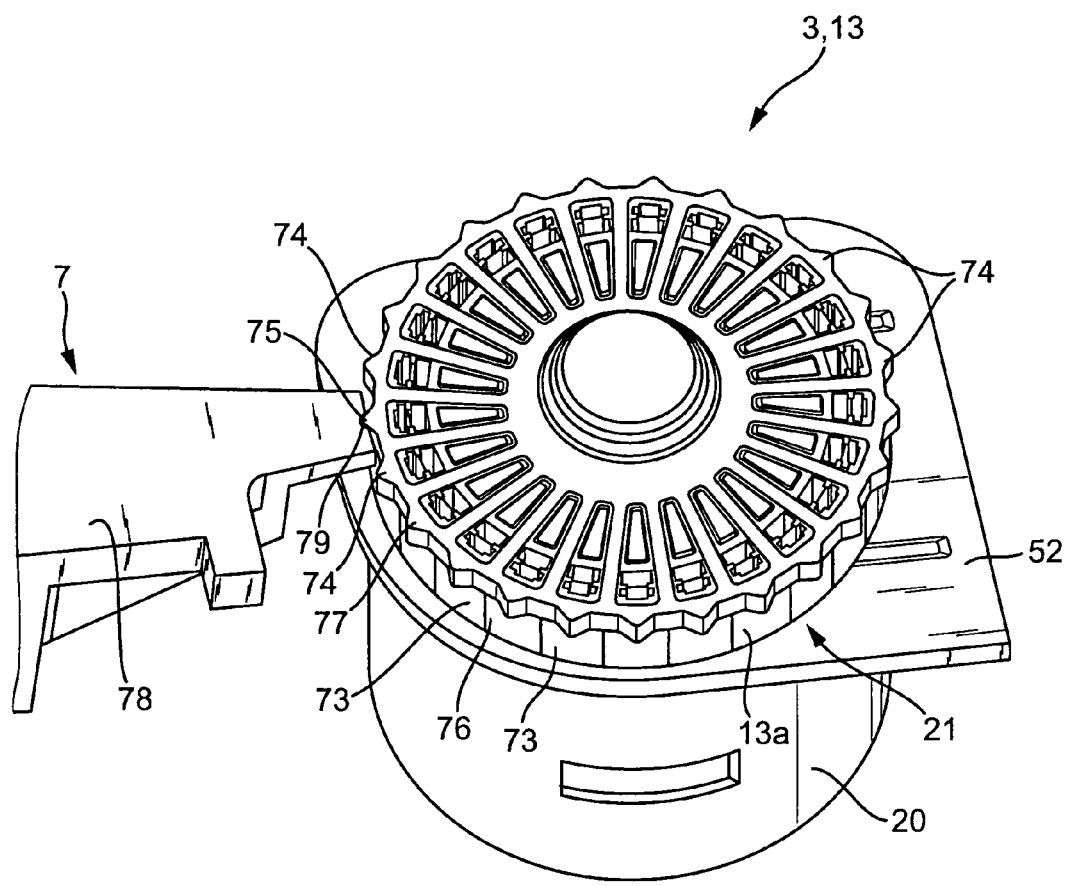
FIG. 9 shows a further embodiment of a magazine.

FIG. 9 shows a further feature of a magazine 3. Positioning elements 74 which facilitate the positioning of the photoelectric measuring unit 7 are positioned in the lateral surface 13a of the analysis element partial magazine 21. The positioning elements 74 may be implemented in the form of teeth 77, for example. The measuring unit has a (movable) positioning arm 78 having a positioning contour 75 on its end, which corresponds with the positioning element 74 of the magazine 3.

The positioning contour 75 implemented as the positioning element receptacle 79 forms the negative mold of a tooth 77, so that the positioning element 74 can be received in the positioning contour 75.

The positioning elements 74 are positioned as on the front end 29 of the analysis element partial magazine 21, so that a peripheral gear ring is formed. They are preferably positioned far enough forward on the front end 29 that the transparent area 73 of the lateral surface 13a remains free. The positioning elements 74 are extruded onto the analysis element partial magazine 21.

A reproducible equal measuring distance between the analysis element 25 and the optic of the measuring unit 7 is ensured by the interaction of positioning element 74 and positioning contour 75. Simultaneously a rotational position fixing is also performed by the gear ring-like implementation of the positioning elements 74. The measuring unit 7, which is (radially) movable perpendicular to the rotational axis, is positioned in the tangential direction of the magazine 3. Axial positioning of measuring unit 7 and analysis element partial magazine 21 to one another is achieved by a suitable implementation of positioning contour 75 and positioning element 74.

The guiding of the measuring unit 7 and its exact positioning (distance and axial position) to the partial magazine 21, in particular their contact connection, ensures an exact and error-free measurement. So as not to corrupt the measurement by a movement of the measuring unit 7 relative to the magazine 3, the contact is produced between measuring unit 7 and magazine 3 before contacting the puncturing element 24 with the analysis element 25, preferably before execution of the lancing procedure, particularly preferably already in the functional position of the magazine 3, i.e., before the connection element 10 of the analysis instrument 2 couples on the puncturing element 24.

By means of the contact between measuring unit 7 and magazine 3, the dimensional tolerances of the individual elements and possible play between the magazine 3 and the mounting 10 of the analysis instrument 2 are partially compensated for, but at least minimized.

The use of positioning elements 74 can also be provided on all magazines 3 described here, of course. It is always suitable in the case of a photometric measurement of the body fluid, because the measuring distance can be set exactly.

In a further embodiment, orientation elements are positioned on the lateral surface 13a of the puncturing element partial magazine 20, which make relative positioning of the two partial magazines 20, 21 to one another easier during the production process of the magazine 3, when the two partial magazines 20, 21 are assembled. A simple and precise relative orientation of the chambers of the two partial magazines 20, 21 can be achieved during the installation with the aid of the orientation elements and the positioning elements 74.

All embodiments of the magazine 3 may be implemented in such a manner that a desiccant chamber 70 is positioned adjacent to each analysis element chamber 23. The desiccant chamber 70 and the analysis element chamber 23 are preferably connected to one another so that an air exchange can occur between the two chambers 70, 23. A desiccant 71 is contained in the desiccant chamber 70 to absorb moisture and keep the analysis element 25 dry.

A second desiccant chamber 72 is preferably contained in the puncturing element partial magazine 20 in the embodiment according to FIGS. 2 and 3. The two aligned chambers 70, 72 form a complete desiccant chamber. If the chambers 70, 72 are separated from one another by a sealing film 28, it is punctured in the production process. Only the desiccant chamber 70 is directly connected to the analysis element chamber 23 so that an air exchange can occur. An exchange between a desiccant chamber 70, 72 and the puncture element chamber 22 is not possible. This embodiment may make more desiccant available to keep the analysis element 25 in the analysis element chamber 23 dry.

The shown embodiments of the magazine 3 according to the present disclosure share the feature that the sequence of the puncture movement is caused by a movement mechanism, which includes the puncturing drive 5. The movement mechanism is implemented so that the individual steps, in particular the movement phases of the puncturing element, occur automatically. An engagement of the user is not necessary. Rather, the user actuates the analysis instrument 2 only at the beginning of the sample acquisition and analysis procedure, after he has laid his finger on the skin contact ring 18. After performing the puncture movement and the analysis, the user can read off the analytical result or a variable corresponding thereto from a display, for example. All required intermediate steps are automatically and independently performed by the analysis instrument. These also include the movement of the magazine 3 into a functional position and the advancing of the magazine 3 in such a manner that after performance of a piercing and an analysis, it is moved into a new functional position, in which the connection element 10 can come into contact with a new, still unused puncturing element 24 and can move the puncturing element 24 on its puncturing path.

While the embodiments have been described as having exemplary designs, the present disclosure may be further modified within the spirit and scope of this disclosure. This application is therefore intended to cover any variations, uses, or adaptations of the invention using its general principles. Further, this application is intended to cover such departures from the present disclosure as come within known or customary practice in the art to which this disclosure pertains.

What is claimed is:
1. An analysis system for determining an analyte in a body fluid sample acquired through a prick in the skin, including:
   a multi-part magazine comprising at least a puncturing element magazine and an analysis element magazine, each having a plurality of chambers, wherein
      in the analysis element magazine, the plurality of chambers are analysis element chambers, which each contain one analysis element, each analysis element having a sample contact zone and a reagent system containing at least one reagent, whose reaction with the sample results in a measurable change of a measuring variable, and
      in the puncturing element magazine, the plurality of chambers are puncturing element chambers, which each contain one puncturing element, each puncturing element having a tip for piercing into the skin, the tip having a capillary channel which forms a fluid connection between the tip and a sample transfer zone of the puncturing element,
   a reusable analysis instrument having
      a puncturing drive for driving a puncture movement of a puncturing element on a movement path, which comprises a propulsion phase in the puncturing direction and, after reaching a reversal point of the puncture movement, a retraction phase opposite to the puncturing direction,
      a mounting for receiving the multi-part magazine in such a manner that one puncturing element chamber of the puncturing element magazine at a time is located in a functional position, in which a puncturing element in the puncturing element chamber can be moved by the puncturing drive, and
      a measuring and evaluation apparatus for measuring the measurable change of the measuring variable and for determining a desired analysis result,
   wherein
      in the functional position of the multi-part magazine, both the puncturing element magazine and the analysis element magazine can be brought into a relative position, in which a puncturing element exit opening of a puncturing element chamber and a puncturing element entry opening of an analysis element chamber are adjacent to one another aligned in such a manner that a puncturing element can be moved from the puncturing element chamber through the puncturing element exit opening of the puncturing element chamber and through the puncturing element entry opening of the adjacent analysis element chamber into the analysis element chamber, the puncturing element entry opening of the analysis element chamber is sealed by means of a sealing film which is opened before or during the puncture movement of the puncturing element from the puncturing element chamber into the analysis element chamber, and the movement path of the puncturing element includes a transfer position in which the sample transfer zone of the puncturing element is positioned adjacent to the sample contact zone of the analysis element, to thereby produce a fluid connection by a relative movement, transverse to the puncturing direction, between the puncturing element and the analysis element to transfer the sample from the puncturing element to the analysis element.

2. A system according to claim 1, wherein the analysis element chamber has a magazine outlet opening, which is sealed by means of a sealing film and which is aligned with the puncturing element entry opening of the analysis element chamber such that the puncturing element can pass through the analysis element chamber and through both the puncturing element entry opening and the magazine outlet opening on the movement path of the puncture movement.

3. A system according to claim 1, wherein each puncturing element chamber has a connection element entry opening and wherein the puncturing element exit opening and the connection element entry opening are both sealed by means of a sealing film.

4. A system according to claim 1, wherein each puncturing element has a coupling structure and the puncturing drive has a coupling element corresponding thereto for bidirectionally coupling puncturing elements with the puncturing drive.

5. A system according to claim 1, wherein each analysis element is positioned in a corresponding analysis element chamber in a fluid transfer position which is fixed in the puncturing direction.

6. A system according to claim 1, wherein at least a part of the propulsion phase of the puncture movement is linear.

7. A system according to claim 1, wherein the sample contact zone of the analysis element includes a surface oriented in the puncturing direction, and the fluid connection is produced by contacting the surface of the sample contact zone of the analysis element with the sample transfer zone of the puncturing element.

8. A system according to claim 1, wherein the relative movement between the puncturing element and the analysis element is caused by a contact pressure element, which when moved transverse to the puncturing direction, presses against the puncturing element located in the transfer position.

9. A system according to claim 8, wherein the contact pressure element is positioned between the puncturing element magazine and the analysis element magazine.

10. A system according to claim 9, wherein the contact pressure element includes guide structures on one of an upper side and a lower side which contact one of the puncturing element magazine and the analysis element magazine.

11. The system according to claim 8, wherein the contact pressure element includes a lower side with a recess facing toward the puncturing element magazine to thereby form a peripheral receptacle chamber around a through opening of the contact pressure element, into which any film parts protruding after opening of the sealing film of the puncturing element exit opening may extend.

12. A system according to claim 1, wherein the relative movement between the analysis element and the puncturing element is caused by a pivot movement of a connection element, which extends through the puncturing element chamber and produces a connection between the puncturing element and the puncturing drive.

13. A system according to claim 1, wherein the analysis element magazine and the puncturing element magazine are movable relative to one another transverse to the puncturing direction.

14. A system according to claim 1, wherein each analysis element chamber is adjacent to a desiccant chamber including a desiccant, the desiccant chamber and the analysis element chamber being connected to one another so that an air exchange takes place between the two chambers.

15. A system according to claim 1, wherein the multi-part magazine is a drum magazine.

16. A system according to claim 1, wherein the measuring and evaluation apparatus comprises a photoelectric measuring unit, and the analysis element magazine has at least one transparent area located such that a change of the measuring variable in an analysis element can be photometrically measured using the photoelectric measuring unit.

17. A system according to claim 1, wherein the capillary channel of each puncturing element extends beyond its sample transfer zone into a sample excess zone and a transfer of the sample only occurs when a first partial quantity of the sample, which is first received after the piercing into the skin in the capillary channel of the puncturing element, has passed the sample transfer zone and is located in the sample excess zone, a second partial quantity of the sample being located in the sample transfer zone.

18. A system according to claim 1, wherein the capillary channel of the puncturing element extends beyond the sample transfer zone into a sample excess zone.

19. The system according to claim 1, wherein the sealing film is glued on the analysis element magazine using hot-melt adhesive in a hot-melt adhesive method, and each opening of the chambers has at a border of the opening a hot-melt adhesive receptacle recess for receiving excess hot-melt adhesive.

20. A multi-part magazine for an analysis instrument, including:

a puncturing element magazine having a plurality of puncturing element chambers, each containing a puncturing element, an analysis element magazine having a plurality of analysis element chambers, each containing an analysis element, wherein each analysis element has a sample contact zone and a reagent system containing at least one reagent, whose reaction with a body fluid results in a measurable change of a measuring variable, and each puncturing element has a tip for piercing into the skin having a capillary channel which forms a fluid connection between the tip and a sample transfer zone of the puncturing element, wherein the multi-part magazine is configured to be received in a mounting of an analysis instrument such that one puncturing element at a time in one of the puncturing element chambers of the multi-part magazine can be moved by a puncturing drive of the analysis instrument on a movement path, which comprises a propulsion phase in the puncturing direction, in order to execute a puncture movement and which comprises a transfer position in which the sample transfer zone of the puncturing element is positioned adjacent to the sample contact zone of the analysis element, to thereby produce a fluid connection by a relative movement, transverse to the puncturing direction, between the puncturing element and the analysis element to transfer the sample from the puncturing element to the analysis element, and wherein the puncturing element magazine and the analysis element magazine are movable relative to one another so that a puncturing element exit opening of a puncturing element chamber and a puncturing element entry opening of an analysis element chamber are adjacent and aligned, the analysis element magazine further including a transparent area, the analysis element being positioned in the analysis element magazine relative to the transparent area in such a manner that a change of a measuring variable in the analysis element can be measured by means of a photoelectric measuring unit, which is positioned outside the multi-part magazine.

21. The multi-part magazine according to claim 20, wherein the multi-part magazine is configured to be moved into a functional position, in which a puncturing element in one of the puncturing element chambers can be moved by the puncturing drive of the analysis instrument in order to execute the puncture movement, and the transparent area of the analysis element magazine is located in front of an optic of the photoelectric measuring unit.

22. The multi-part magazine according to claim 20, wherein the analysis element magazine further includes a positioning element, and the photoelectric measuring unit has a positioning contour, which cooperates with the positioning element to position the transparent area of the analysis element magazine relative to the measuring unit.

23. A method for producing a multi-part magazine according to claim 20, including the steps of:

a) equipping the puncturing element magazine with puncturing elements;
b) sealing a puncturing element exit opening of each puncturing element chamber with a film;
c) sealing a connection element entry opening of each puncturing element chamber with a film;
d) sterilizing the puncturing elements in the puncturing element magazine;
e) connecting the puncturing element magazine and the analysis element magazine;
f) sealing a puncturing element entry opening of each analysis element chamber of the analysis element magazine with a film;
g) equipping the analysis element magazine with analysis elements; and
h) sealing a magazine outlet opening of each analysis element chamber of the analysis element magazine with a film.

24. The method according to claim 23, further including the step of:

introducing a desiccant into a desiccant chamber in such a manner that the desiccant can absorb moisture from an analysis element chamber.

25. The method according to claim 23, wherein the sterilizing step is performed by irradiation by means of beta radiation.

26. The multi-part magazine according to claim 20, wherein the relative movement being one of (a) relative movement between the puncturing element and the analysis element caused by a contact pressure element positioned in the puncturing direction between the puncturing element magazine and the analysis element magazine, which when moved transverse to the puncturing direction, presses against the puncturing element, (b) relative movement between the puncturing element and the analysis element caused by a pivot movement of a connection element connecting the puncturing element and the puncturing drive, and (c) relative movement between the puncturing element magazine and the analysis element magazine relative to one another traverse to the puncturing direction.

27. A multi-part magazine for an analysis instrument, including:

a puncturing element magazine having a plurality of puncturing element chambers, each containing a puncturing element, an analysis element magazine having a plurality of analysis element chambers, each containing an analysis element, wherein each analysis element has a sample contact zone and a reagent system containing at least one reagent, whose reaction with a body fluid results in a measurable change of a measuring variable, and each puncturing element has a tip for piercing into the skin having a capillary channel which forms a fluid connection between the tip and a sample transfer zone of the puncturing element, wherein the multi-part magazine is implemented for being received in a mounting of an analysis instrument in such a manner that one puncturing element at a time in one of the puncturing element chambers of the multi-part magazine can be moved by a puncturing drive of the analysis instrument on a movement path, which comprises a propulsion phase in the puncturing direction, in order to execute a puncture movement, wherein the puncturing element magazine and the analysis element magazine are movable relative to one another so that a puncturing element exit opening of a puncturing element chamber and a puncturing element entry opening of an analysis element chamber are adjacent to one another aligned in such a manner that one puncturing element can be moved from the puncturing element chamber through its puncturing element exit opening and through the puncturing element entry opening of the adjacent analysis element chamber into the analysis element chamber and into a transfer position in which the sample transfer zone of the puncturing element is positioned adjacent to the sample contact zone of the analysis element, to thereby produce a fluid connection by a relative movement, transverse to the puncturing direction, between the puncturing element and the analysis element to transfer the sample from the puncturing element to the analysis element, and the puncturing element entry opening of the analysis element chamber is sealed by means of a sealing film, which is positioned and implemented to be opened before or during the puncture movement of the puncturing element from the puncturing element chamber into the analysis element chamber.

28. The multi-part magazine according to claim 27, wherein each puncturing element chamber has a connection element entry opening, which is sealed by means of a sealing film.

29. The multi-part magazine according to claim 27, wherein each analysis element is positioned in a corresponding analysis element chamber in a fluid transfer position which is fixed in the puncturing direction.

30. The multi-part magazine according to claim 27, wherein the relative movement between the analysis element and the puncturing element is caused by a pivot movement of a connection element, which extends through the puncturing element chamber and produces a connection between the puncturing element and the puncturing drive.

31. The multi-part magazine according to claim 27, wherein the analysis element magazine and the puncturing element magazine are movable relative to one another transverse to the puncturing direction.

32. The multi-part magazine according to claim 27, wherein the multi-part magazine is a drum magazine.

33. The multi-part magazine according to claim 27, wherein the capillary channel of the puncturing element extends beyond the sample transfer zone into a sample excess zone.

34. The multi-part magazine according to claim 27, wherein the sealing film is glued on the analysis element magazine using hot-melt adhesive in a hot-melt adhesive method, and each opening of the chambers has at a border of the opening a hot-melt adhesive receptacle recess for receiving excess hot-melt adhesive.

35. The multi-part magazine according to claim 27, wherein the relative movement is caused by a relative movement between the puncturing element and the analysis element caused by a contact pressure element positioned in the puncturing direction between the puncturing element magazine and the analysis element magazine, which when moved transverse to the puncturing direction, presses against the puncturing element.

* * * * *